(12) United States Patent
Terasawa et al.

(10) Patent No.: US 7,337,008 B2
(45) Date of Patent: Feb. 26, 2008

(54) VISUAL RESTORATION AIDING DEVICE

(75) Inventors: Yasuo Terasawa, Obu (JP); Hiroyuki Tashiro, Fukuoka (JP); Kenzo Shodo, Kyoto (JP); Jun Ohta, Nara (JP); Takashi Tokuda, Kyoto (JP); Keiichiro Kagawa, Ikoma (JP); Akihiro Uehara, Nara (JP); Toru Yagi, Nagoya (JP)

(73) Assignee: Nidek Co., Ltd., Gamagori-Shi (JP)

(*) Notice: Subject to any disclaimer, the term of this patent is extended or adjusted under 35 U.S.C. 154(b) by 0 days.

(21) Appl. No.: 10/876,530

(22) Filed: Jun. 28, 2004

(65) Prior Publication Data

US 2005/0004626 A1    Jan. 6, 2005

(30) Foreign Application Priority Data

Jul. 1, 2003    (JP) .............................. 2003-189830

(51) Int. Cl.
 *A61N 1/18* (2006.01)
(52) U.S. Cl. ..................................................... 607/54
(58) Field of Classification Search .................. 607/53, 607/54, 116; 623/6.63
 See application file for complete search history.

(56) References Cited

U.S. PATENT DOCUMENTS

| | | | | |
|---|---|---|---|---|
| 5,024,223 A | * | 6/1991 | Chow | .......................... 607/53 |
| 5,935,155 A | * | 8/1999 | Humayun et al. | ............. 607/54 |
| 6,368,349 B1 | * | 4/2002 | Wyatt et al. | ............... 623/6.63 |
| 6,427,087 B1 | * | 7/2002 | Chow et al. | .................. 607/54 |
| 6,804,560 B2 | * | 10/2004 | Nisch et al. | .................. 607/54 |
| 2002/0038134 A1 | * | 3/2002 | Greenberg et al. | ............. 607/1 |

FOREIGN PATENT DOCUMENTS

| | | |
|---|---|---|
| JP | A 8-511697 | 12/1996 |
| JP | A 11-506662 | 6/1999 |
| JP | A 11-511248 | 9/1999 |
| JP | A 2002-505910 | 2/2002 |
| WO | WO 94/26209 | 11/1994 |
| WO | WO 96/39221 | 12/1996 |
| WO | WO 97/05922 | 2/1997 |
| WO | WO 02/080828 A1 | 10/2002 |

* cited by examiner

*Primary Examiner*—Mark Bockelman
*Assistant Examiner*—Eric D. Bertram
(74) *Attorney, Agent, or Firm*—Oliff & Berridge, PLC

(57) ABSTRACT

A visual restoration aiding device for restoring vision of a patient comprises: a plurality of substrates which are placed on or under a retina of a patient's eye; a plurality of electrodes which are mounted on each substrate to apply an electrical stimulation pulse signal to cells constituting the retina; and a connecting unit which has flexibility and connects the substrates.

3 Claims, 5 Drawing Sheets

VISUAL RESTORATION AIDING DEVICE

BACKGROUND OF THE INVENTION

1. Field of the Invention

The present invention relates to a visual restoration aiding device for inducing restoration of vision.

2. Description of Related Art

In recent years, there have been researches about a visual restoration aiding device using an electrode or the like placed (implanted) in an eye to induce restoration of vision by electrically stimulating cells constituting a retina. As such visual restoration aiding device, there has been proposed, for example, a device designed to convert an extracorporeally photographed visual image to an optical signal or an electromagnetic signal, transmit the converted signal into the eye, and then output an electrical stimulation pulse signal (a stimulating electric current) through a plurality of electrodes mounted (provided) on a substrate placed in the eye to stimulate the cells constituting the retina to induce visual restoration (see U.S. Pat. No. 5,935,155). To provide a wider visual field, the electrical stimulation need be applied to the retina in as large an area as possible.

To apply the electrical stimulation to the retina in a large area through the electrodes, it is necessary to provide a large substrate for mounting thereon the electrodes. However, as the substrate has a larger area, the substrate has to be bent more largely along a curved surface of the retina to bring the electrodes into close contact with the retina. This would be difficult.

SUMMARY THE INVENTION

The present invention has been made in view of the above circumstances and has an object to overcome the above problems and to provide a visual restoration aiding device capable of applying electrical stimulation to a retina in a large area.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a visual restoration aiding device for restoring vision of a patient, comprising: a plurality of substrates which are placed on or under a retina of a patients eye; a plurality of electrodes which are mounted on each substrate to apply an electrical stimulation pulse signal to cells constituting the retina; and a connecting unit which has flexibility and connects the substrates.

According to another aspect, the invention provides a visual restoration aiding device for restoring vision of a patient, comprising: a substrate which is placed on or under a retina of a patient's eye, the substrate being constructed of a combination of a plurality of long, narrow substrates; and a plurality of electrodes which are mounted on the substrate to apply an electrical stimulation pulse signal to cells constituting the retina.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
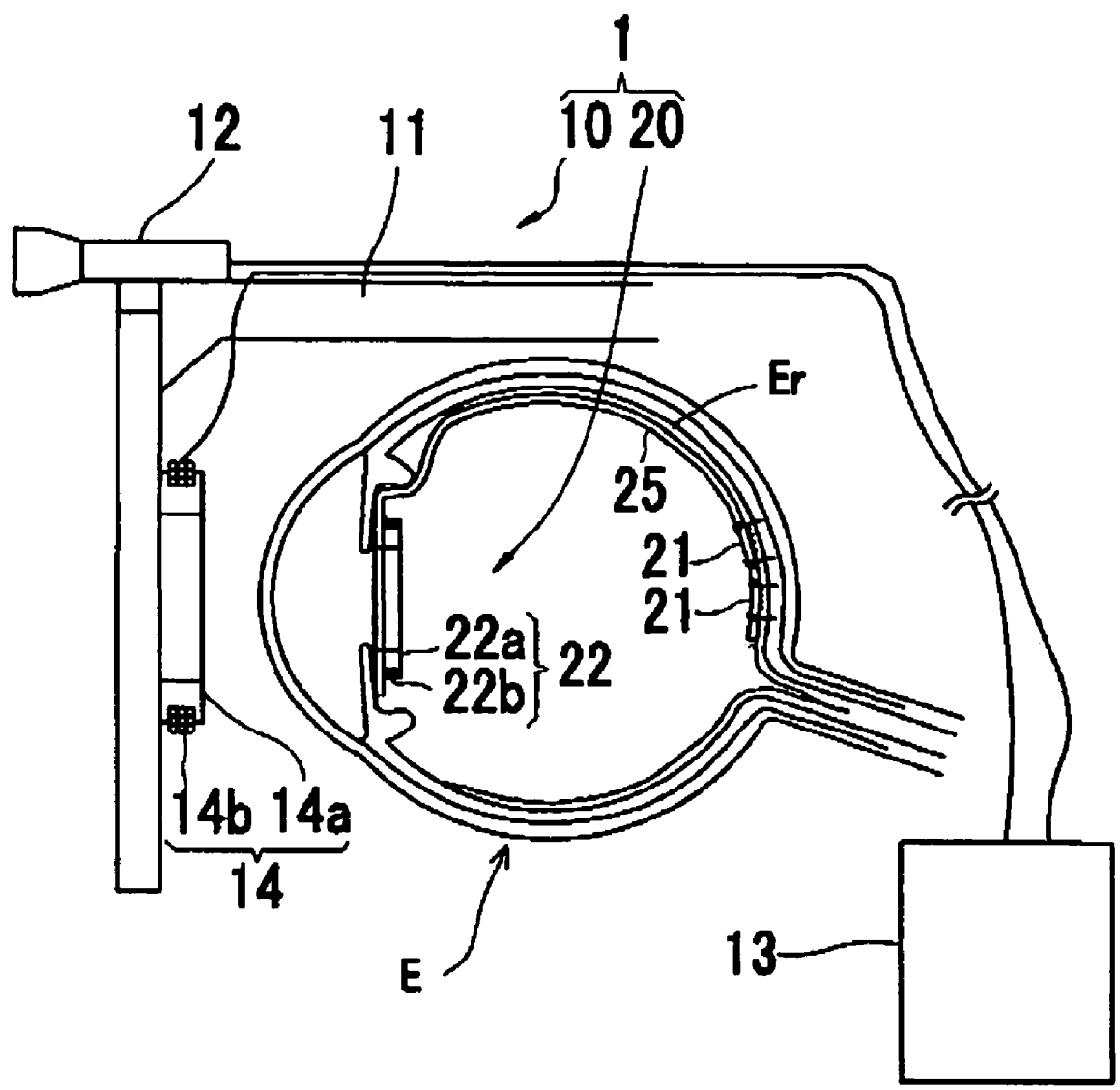
FIG. 1 is a schematic structural view of a visual restoration aiding device in an embodiment according to the present invention.
Figure 2:
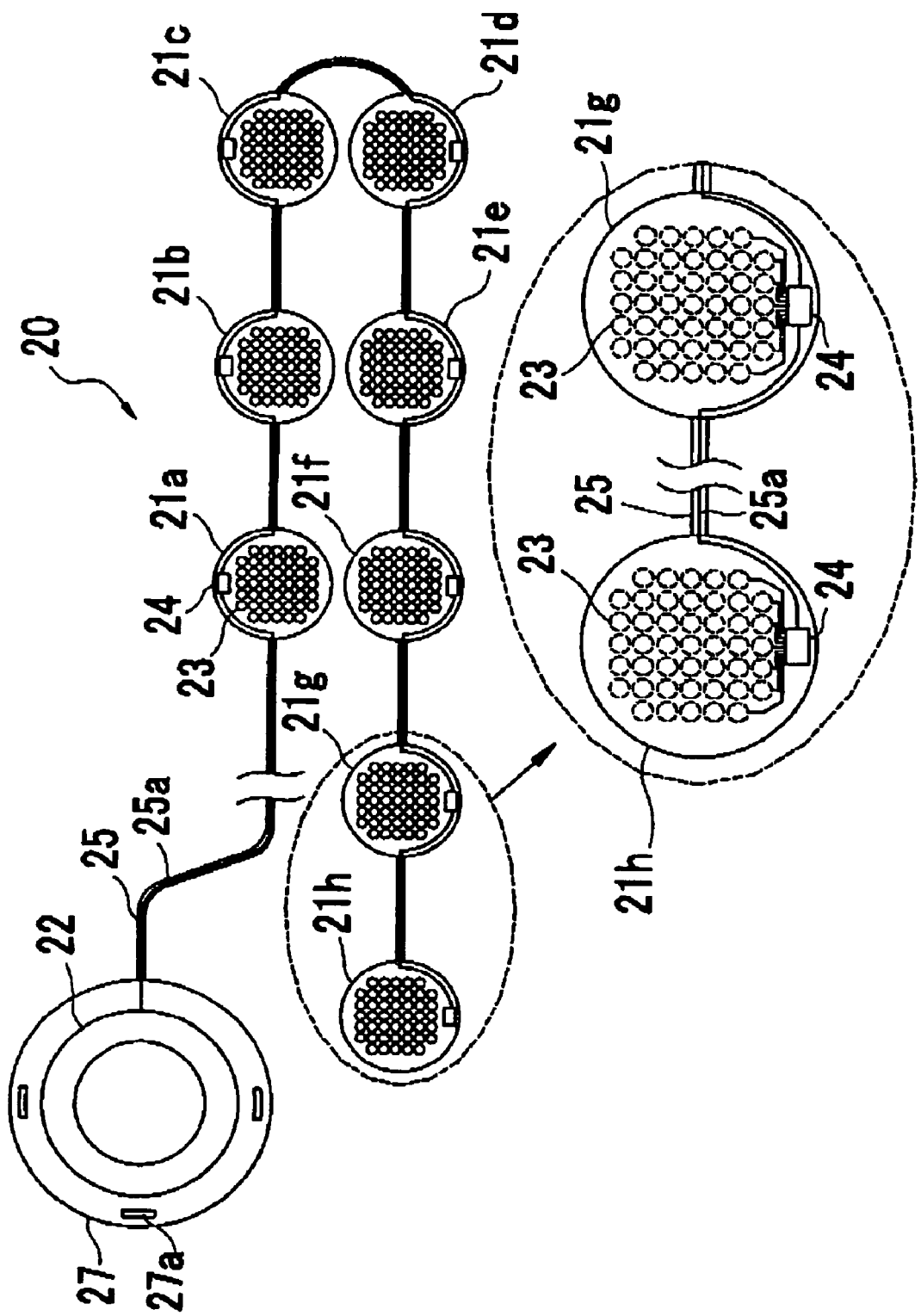
FIG. 2 is a schematic structural view of an internal device.
Figure 3:
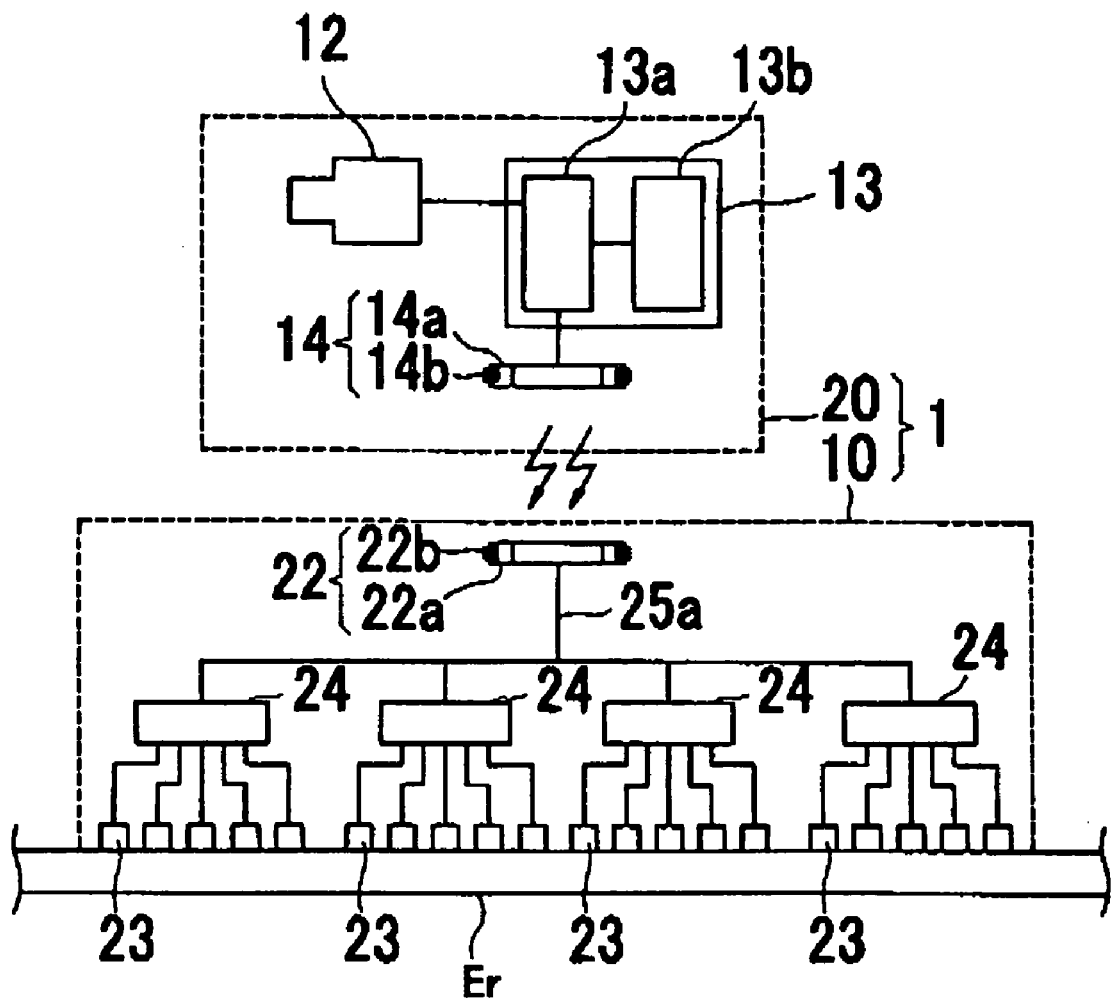
FIG. 3 is a block view showing a control system of the visual restoration aiding device.

A detailed description of a preferred embodiment of a visual restoration aiding device embodying the present invention will now be given referring to the accompanying drawings. FIG. 1 is a schematic structural view of the visual restoration aiding device in the present embodiment. FIG. 2 is a schematic structural view (including a partially enlarged view) of an internal device. FIG. 3 is a schematic block diagram of a control system in the visual restoration aiding device.

The visual restoration aiding device 1 includes an external (extracorporeal) device 10 which photographs the outside world, or captures surrounding images, and an internal (intracorporeal) device 20 which applies electrical stimulation to cells constituting a retina to induce restoration of vision. The external device 10 includes a visor 11 which a patient wears, a photographing unit 12 such as a CCD camera which is mounted on the visor 11, an external unit 13, and a transmitting unit 14 including a coil. The visor 11 is shaped like eyeglasses, which the patient wears in the front of his eye E. The photographing unit 12 is mounted in the front of the visor 11 and photographs an object to be recognized by the patient.

The external unit 13 includes a pulse signal converting unit 13a for converting photographic data (video data) transmitted from the photographing unit 12 to data (information) for electrical stimulation pulse signals and a power unit 13b for supplying electric power to the visual restoration aiding device 1 (that is, the external device 10 and the internal device 20). The transmitting unit 14 includes a ring-shaped magnetic core 14a and a primary coil 14b wound around the magnetic core 14a. The magnetic core 14a is made of a material generally used for a magnetic substance, such as ferrite. The primary coil 14b is made of a material generally used for a coil wire, such as copper, gold, or platinum. The transmitting unit 14 is used for transmitting the converted data for electrical stimulation pulse signals by the converting unit 13a and the electric power for driving the internal device 20, in the form of electromagnetic waves, to the internal device 20 by wireless communication.

The internal device 20 includes a plurality of substrates 21 (21a-21h) on each of which many electrodes 23 are mounted (arranged) for applying the electrical stimulation pulse signals to the cells constituting the retina Er of the eye E, a receiving unit 22 including a coil for receiving the electromagnetic waves from the external device 10, and a connecting unit 25 which connects the substrates 21 and connects each substrate 21 to the receiving unit 22. The receiving unit 22 includes a ring-shaped magnetic core 22a and a secondary coil 22b wound around the magnetic core 22a. The magnetic core 22a is made of a material generally used for a magnetic substance, such as ferrite. The secondary coil 22b is made of a material generally used for a coil wire, such as copper, gold, or platinum.

The receiving unit 22 is mounted on a base 27 having openings 27a formed in a circumferential portion at circumferentially spaced points where each opening 27a will not cause dynamic damage of an iris of the eye E when the base 27 is set on the back side of the iris. Each opening 27a is utilized for sewing the base 27 on the iris, thereby fixedly attaching the internal device 20 in the eye E.

The substrate 21 is made of a substrate material such as silicon, glass, etc., coated with a material having good biocompatibility, such as polyimide. It is to be noted that the whole substrate 21 may be made of only a material having good biocompatibility, such as polyimide. The substrate 21 is of a circular plate having a diameter of about 0.1 mm to about 5.0 mm. On the under surface of the substrate 21 (i.e., on the back of the drawing sheet of FIG. 2), a plurality of electrodes 23 are mounted (arranged) at predetermined intervals. The electrodes 23 in the present embodiment are arranged at regular intervals, but not limited thereto. For instance, the electrodes 23 of each substrate 21 may be arranged at predetermined intervals according to a position of placement of each electrode 23 on the retina Er, a shape of the substrate 21, and other conditions, so that the electrodes 23 are spaced closely in part and thinly in another part on one substrate 21.

Each electrode 23 has a diameter of about 50 μm to about 500 μm. The plurality of electrodes 23 are mounted on the substrate 21, forming a multipoint electrode array. In the present embodiment, forty-five electrodes 23 are mounted on one substrate 21, but not limited thereto. Instead of the multipoint electrode array, another configuration that a single electrode 23 is mounted on one substrate 21 may be adopted.

Figure 4:
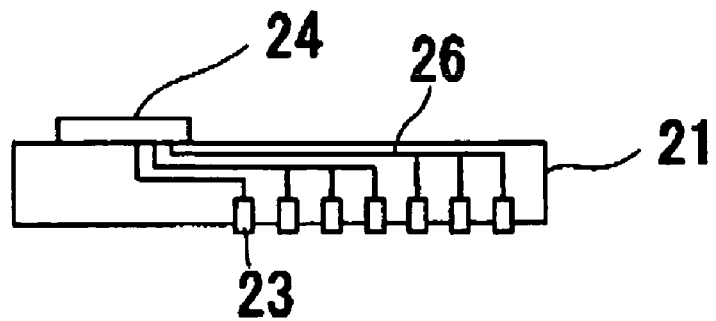
FIG. 4 is a view showing one example of electrical connection between electrodes and an internal unit.

Each electrode 23 is connected with an independent electric wire (a lead wire) 26. As shown in FIG. 4, each electric wire 26 connects between the associated electrode 23 and the internal unit 24 formed of a demultiplexer mounted (provided) on the upper surface of the substrate 21 (i.e., on the front of the drawing sheet of FIG. 4). In FIG. 4, for convenience, some electric wires are seemingly used to singly connect more than one electrode 23 to the internal unit 24. The internal unit 24 is also connected to the receiving unit 22 through en electric wire 25a contained in the connecting unit 25. The internal unit 24 includes a converting circuit for converting the data for electrical stimulation pulse signals transmitted via the receiving unit 22 to the electrical stimulation pulse signals and a control part which controls output of the electrical stimulation pulse signals through the electrodes 23.

If the electrodes 23 are individually connected to the internal unit 24, as mentioned above, the wiring in a limited area may be difficult depending on the number of electrodes 23. In this case, as shown in FIG. 4, the electric wire 26 is preferably provided in multi-layered wiring, allowing the electrodes 23 to be individually connected to the internal unit 24. The substrate 21 of the multi-layered wiring can be formed by alternately arranging wiring layers and insulating layers.

In the present embodiment, the base 27 mounting thereon the receiving unit 22 is connected to eight substrates 21a to 21h in sequence (in series) through the connecting unit 25. The receiving unit 22 is thus electrically connected to eight internal units 24 through the electric wire 25a. The connecting unit 25 is made of a flexible material such as resin and bonded to each substrate 21 with adhesive or by welding. The thus connected substrates 21a to 21h can be bent freely at respective associated portions of the connecting unit 25. Accordingly, while ensuring electrical connection to each substrate 21 (each internal unit 24), the positional relationship between the substrates 21 can be changed freely to be placed on the retina Er.

The internal device 20 is entirely coated with an insulating material having good biocompatibility such as polyimide to prevent infiltration of bodily fluid and the like into the internal device 20. The electrodes 23 are exposed from the coating surface in order to directly touch the retina Er. The electrodes 23 are formed in an exposed state from the coating surface in the following steps of: (1) making each electrode 23 by use of an electrode material such as gold, platinum, or the like at a predetermined position corresponding to the end of the electric wire 26; (2) connecting the substrates 21 through the connecting unit 26, electrically connecting the internal devices 24 through the electric wire 25a, and coating each substrate 21 and the connecting unit 25 with an insulating material having good biocompatibility; and (3) removing the coating of each electrode 23 by laser irradiation or other techniques to expose each electrode 23. In the above manner, the exposed electrode 23 can be produced.

Figure 5:
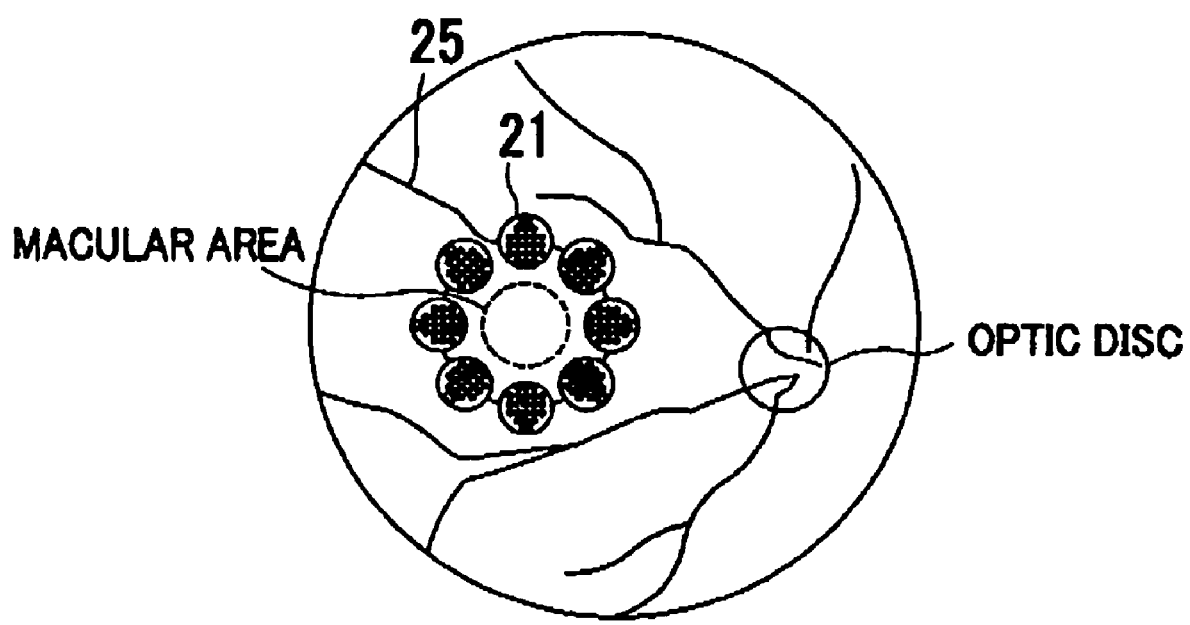
FIG. 5 is a view showing an example the internal device placed on a retina.

To place the substrates 21 in the eye E, for example, the substrates 21 are fixed onto the retina Er with a rivet-shaped tack not shown, a good biocompatible adhesive, or the like. For example, as shown in FIG. 5, the substrates 21a to 21h are placed on the retina Er around the macular area (or the central fovea) of the eye E.

Although the independent substrates 21 in the present embodiment are connected in series through, the connecting unit 26, the following alternatives may be adopted. For instance, the plurality of substrates 21 each having the circular plate shape sa mentioned above and the connecting unit 25 may be integrally formed. Another alternative is that a plurality of substrates 21 are radially connected to one substrate 21, instead of connecting the substrates 21 in series. Further, an indifferent electrode may be provided in the internal device 20 to efficiently output the electrical stimulation pulse signal through each electrode 23.

The following explanation is made on output control of the electrical stimulation pulse signals for visual restoration in the visual restoration aiding device 1 constructed as above. The external device 10 and the internal device 20 are respectively attached outside and inside the eye E as shown in FIGS. 1 and 5.

The photographic data on an object photographed by the photographing unit 12 is converted by the signal converting unit 13a to the data for electrical stimulation pulse signals within a predetermined frequency band. The converted data is then transmitted in the form of electromagnetic waves by the transmitting unit 14 to the internal device 20. The data for electrical stimulation pulse signals includes the designating information about the substrates 21 (21a to 21h) and the designating information about the electrodes 23 needed to output the electrical stimulation pulse signals, the stimulation conditions such as a frequency of the electrical stimulation pulse signals to be outputted through the electrodes 23, an amplitude (namely, intensity of stimulation electric currents), and a stimulating time length. Simultaneously, the signal converting unit 13a converts the electric power supplied from the power unit 13b to an electric power signal of a frequency band different from the frequency band of the data for electrical stimulation pulse signals and transmits it in the form of electromagnetic waves to the internal device 20.

In the internal device 20, the receiving unit 22 receives the data for electrical stimulation pulse signals and the data for electric power transmitted from the external device 10 and then transmits the same signals to each of the internal units 24 mounted on the substrates 21 through the electric wire 25a of the connecting unit 25. Each internal unit 24 extracts a signal of the frequency band being used for the data for electrical stimulation pulse signals from among the received signals. A signal of another frequency band is supplied as the electric power for driving the internal device 20.

The data for electrical stimulation pulse signals includes the designating information about the substrate(s) 21 and the designating information about the electrode(s) 23. If the data for electrical stimulation pulse signals extracted by the internal unit 24 includes the substrate designating information that designates the associated substrate 21, the internal unit 24 in that substrate 21 outputs the electrical stimulation pulse signal(s) through the electrode(s) 23 designated in the electrode designating information based on the data for electrical stimulation pulse signals. If the data for electrical stimulation pulse signals extracted by the internal unit 24 does not include the substrate designating information that designates the associated substrate 21, the internal unit 24 does not output the electrical stimulation pulse signal(s) from any electrodes 23.

Because the visual restoration aiding device in the present embodiment uses the plurality of substrates 21, it is necessary to accurately grasp the information on the position of each substrate 21 placed on the retina Er. The position of each substrate 21 is checked as follows: an electrical stimulation pulse signal is outputted through one or plural electrodes 23 in a specified substrate 21, an operator grasps what vision a patient obtains in response to the output of the electrical stimulation pulse signal, and the operator feeds back the obtained visual information as correcting information to the signal converting unit 13a. This procedure is repeated with respect to all the substrates 21 and the electrodes 23 placed on the retina Er. Thus, the correcting information can be obtained to be used for converting the photographic data to the data for electrical stimulation pulse signals.

In the above manner, the plurality of small substrates are placed on the retina in a large area, so that electrical stimulation can be applied to the retina in the large area, with the result that the patient can obtain the vision of a wider visual field and a high resolution. Further, as compared with the use of a single large substrate through which electrical stimulation is applied to the retina in a large area, each electrode in the present embodiment can be placed in closer contact with the retina, thus more efficiently applying electrical stimulation to the retina. Insertion of the internal device 20 in the eye is also easy. The number of electrodes mounted on one substrate may be small, so that enough space can be provided for wiring to each electrode. In addition, such a smaller substrate resists cracking.

In the present embodiment, eight substrates 21 are placed on the retina Er, but not limited thereto. More substrates 21 may be placed spirally on the retina Er to apply electrical stimulation in a larger area.

Figure 6:
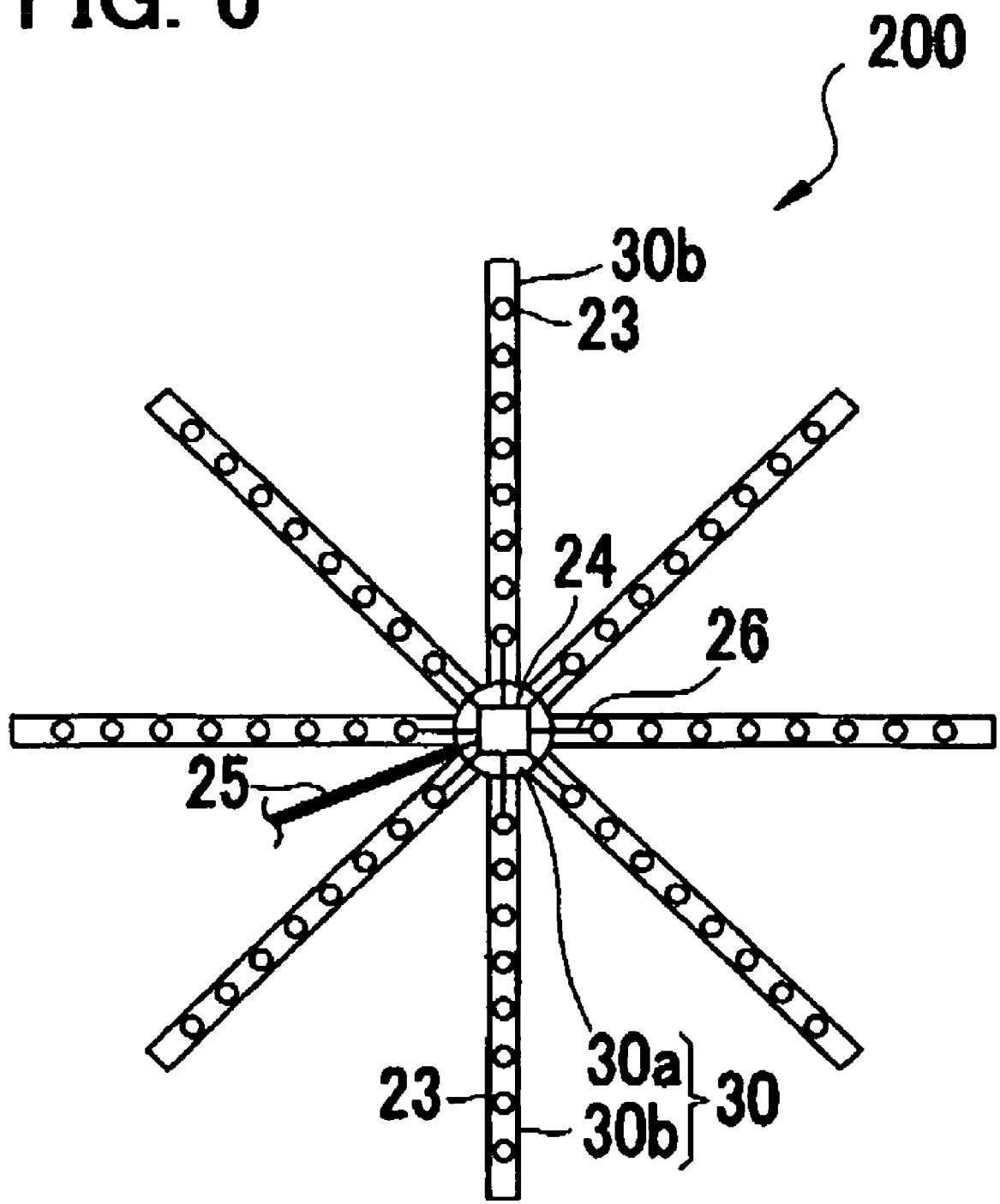
FIG. 6 is a schematic structural view of a modification example of the internal device.

A modification example of the internal device will be explained below. FIG. 6 is a schematic structural view of an internal device 200.

A substrate 30 constituting part of the internal device 200 includes a first substrate 30a on which an internal unit 24 is mounted and a plurality of second substrates 30b of a long, narrow strip shape, on which a plurality of electrodes 23 are mounted (arranged). An end of each of the second substrates 30b is fixed to the first substrate 30a, while the other end is so free as to be bent along the retina Er. In the present embodiment, the substrates 30b are arranged to radially extend from the substrate 30a at predetermined circumferential intervals, namely, arranged in a radial pattern.

On the back of each substrate 30b (i.e., on the back of the drawing sheet of FIG. 6), a plurality of electrodes 23 are mounted, each being connected to an electric wire 26 extending from the internal unit 24 mounted on the front of the substrate 30a. The electric wire 26 is constructed in multi-layered wiring as with the electric wire 26 in the aforementioned example. The substrate 30a is bonded to the connecting unit 25 whose end is connected to the receiving unit 22 (the base 27). The substrate 30 can be produced by cutting long narrow strips from a flat plate made of the aforementioned substrate material. Further, the first substrate 30a and the second substrates 30b may be produced in a manner that separately molds the first and second substrates 30a and 30b or cuts them from the flat plate, and bonds them together.

When the substrate 30 is placed on the retina Er, each substrate 30b formed in the shape of a long narrow strip can be easily bent along the curved surface of the retina Er. Consequently, each electrode 23 can be placed in close contact with the retina Er in a large area, thereby applying the electrical stimulation to the retina Er in the large area. In this example, the substrate 30 is constructed of a combination of the second substrates 30b arranged in a radial pattern around the first substrate 30a, but not limited thereto. For example, a key pattern, a netted pattern, or other patterns may be adopted.

Although the substrates 21 and 30 in the above embodiment are placed on the retina Er, the present invention may be applied to a visual restoration aiding device that the substrates 21 and 30 are placed under the retina Er (between the retina and choroid).

In the above embodiment, the data for electrical stimulation pulse signals is produced hosed on the photographic data transmitted from the extracorporeally disposed photographing unit 12 and is transmitted together with electric power to the internal device 20. The present invention can be applied not only to the above structured device but also to another visual restoration aiding device of an intracorporeally photographing type constructed of a photodiode array in which a light intensity detecting unit (a light receiving element) formed of a photodiode and a pulse signal generating circuit are formed on a substrate and one electrode is provided in correspondence with one light receiving element.

In the visual restoration aiding device of the intracorporeally photographing type, for example, the aforementioned photodiode array is used as a unit and two or more photodiode arrays are connected. It is to be noted that this visual restoration aiding device of the intracorporeally photographing type is constructed such that the electrical stimulation pulse signal is changed through the pulse signal generating circuit based on the light intensity detected by the light receiving element to convert an image to be projected onto the retina to the electrical stimulation pulse signal.

Further, the visual restoration aiding device of the intracorporeally photographing type does not need the extracorporeally set photographing unit mentioned above. Accordingly, the aforementioned transmitting unit 14 and receiving unit 22 may be utilized to transmit power supply and control correcting information. A power supply part may be provided in a substrate so that the aforementioned transmitting unit 14 and receiving unit 22 are utilized only for supplying the date for electrical stimulation pulse signals.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A visual restoration aiding device for restoring vision of a patient, comprising:
    a communication unit which transmits data for an electrical stimulation pulse signal by converting photographic data obtained by a photographing unit outside a patient's eye to the electrical stimulation pulse signal data;
    a receiving unit which receives the electrical stimulation pulse signal data transmitted from the communication unit;
    a plurality of substrates which are adapted to be placed in the patient's eye;
    a connecting unit which has flexibility and connects the substrates to one another;
    a plurality of electrodes which are mounted on one surface of each substrate to apply the electrical stimulation pulse signal to cells constituting a retina;
    a plurality of control units, each of which is provided on the other surface of each substrate and is electrically connected to the receiving unit and each electrode mounted on the associated substrate, each control unit controlling output of the electrical stimulation pulse signal through each electrode based on the electrical stimulation pulse signal data received by the receiving unit; and
    wherein the communication unit converts the photographic data to the electrical stimulation pulse signal data including designating information on a substrate and an electrode, and an electrical stimulation condition, and
    the communication unit has correcting information determined by taking account of a position of the substrate placed in the patient's eye as correcting information used for converting the photographic data to the electrical stimulation pulse signal data, the correcting information being determined by feeding back in advance visual information obtained when the electrical stimulation pulse signal is output from a specified electrode of a specified substrate, the designating information being determined based on the correcting information.

2. The visual restoration aiding device according to claim 1, wherein each substrate is of a circular plate shape having a diameter of approx. 0.1 mm to approx. 5.0 mm.

3. The visual restoration aiding device according to claim 1, wherein the connecting unit connects the substrates in series.

* * * * *